United States Patent [19]

Deras

[11] Patent Number: 5,088,985
[45] Date of Patent: Feb. 18, 1992

[54] SAFETY SYRINGE

[76] Inventor: Marco A. Deras, 4820 SE. 41st, Del City, Okla. 73115

[21] Appl. No.: 561,080

[22] Filed: Aug. 1, 1990

[51] Int. Cl.⁵ .............................................. A61M 5/32
[52] U.S. Cl. .................................... 604/192; 604/263; 604/198; 604/905; 128/919
[58] Field of Search ............... 604/192, 193, 194, 197, 604/198, 263, 905, 110, 411–415; 128/919

[56] References Cited

U.S. PATENT DOCUMENTS

| | | | |
|---|---|---|---|
| 2,578,394 | 12/1951 | Blackman | 604/194 |
| 3,040,743 | 6/1962 | Naess | 128/216 |
| 3,107,785 | 10/1963 | Roehr | 604/194 X |
| 3,534,734 | 10/1970 | Budreck | 604/194 |
| 3,993,063 | 11/1976 | Larrabee | 128/215 |
| 4,011,868 | 3/1977 | Friend | 604/194 |
| 4,356,822 | 11/1982 | Winstead-Hall | 128/215 |
| 4,390,016 | 6/1983 | Riess | 604/236 |
| 4,417,887 | 11/1983 | Koshi | 604/162 |
| 4,425,120 | 1/1984 | Sampson et al. | 604/198 |
| 4,659,330 | 4/1987 | Nelson et al. | 604/192 |
| 4,664,259 | 5/1987 | Landis | 206/365 |
| 4,664,653 | 5/1987 | Sagstetter et al. | 604/197 |
| 4,681,567 | 7/1987 | Masters et al. | 604/198 |
| 4,702,738 | 10/1987 | Spencer | 604/198 |
| 4,702,739 | 10/1987 | Milorad | 604/198 |
| 4,723,943 | 2/1988 | Spencer | 604/198 |
| 4,725,267 | 2/1988 | Vaillancourt | 604/192 |
| 4,735,618 | 4/1988 | Hagen | 604/192 |
| 4,737,144 | 4/1988 | Choksi | 604/198 |
| 4,738,663 | 4/1988 | Bogan | 604/198 |
| 4,752,290 | 6/1988 | Schramm | 604/198 |
| 4,762,516 | 8/1988 | Luther et al. | 604/164 |
| 4,834,716 | 5/1989 | Ogle | 604/192 |
| 4,863,433 | 9/1989 | Payne et al. | 604/194 |
| 4,932,940 | 6/1990 | Walker et al. | 604/110 |
| 4,946,445 | 8/1990 | Lynn | 604/192 |
| 4,968,304 | 11/1990 | Alter et al. | 604/192 |
| 4,994,044 | 2/1991 | LoDucca | 604/192 |
| 4,998,712 | 3/1991 | Vailencourt | 604/283 |
| 4,998,925 | 3/1991 | Al-Sioufi et al. | 604/283 |
| 4,998,927 | 3/1991 | Vaillancourt | 604/283 |
| 5,011,475 | 4/1991 | Olson | 604/192 |

FOREIGN PATENT DOCUMENTS

476501  9/1969  Switzerland ............... 604/192

Primary Examiner—C. Fred Rosenbaum
Assistant Examiner—Mark O. Polutta
Attorney, Agent, or Firm—Laney, Dougherty, Hessin & Beavers

[57] ABSTRACT

A safety syringe having both apparatus for shielding the needle and apparatus for removing the needle after it is used. The apparatus for removing the needle is an elongated member that includes means for grasping the needle and removing it from the syringe body. An elongated cavity is disposed in the extension arm extending from the piston member of the syringe for receiving and storing the apparatus for removing the needle. The apparatus for shielding the needle is a cylindrical member that is attached over the syringe body and movable to and from an extended position over the needle. The safety syringe prevents inadvertent exposure of the needle prior to, during and after use of the syringe.

18 Claims, 2 Drawing Sheets

SAFETY SYRINGE

BACKGROUND OF THE INVENTION

1. Field of the Invention

This invention relates generally to syringes, and more particularly, but not by way of limitation, to hypodermic syringes that include apparatus for preventing exposure of the needle to people coming into contact therewith.

2. Background of the Invention

Many problems and injuries are associated with conventional hypodermic syringes due to human contact with the needle. Contact with the needle before it is used can contaminate the needle and any medication therein. Contact with the needle after it is used can result in the transmission of disease.

A conventional hypodermic syringe includes a syringe body, a piston member, a hypodermic needle and a needle cap. The needle cap is a tubular member removably attached to the needle hub over the sharp end of the needle. Due to the spread of infectious diseases such as hepatitis B and acquired immune deficiency syndrome (aids), most hypodermic syringes used today are designed for one use only and immediate disposal.

Although disposal of hypodermic syringes immediately after they are used reduces human exposure to contaminated needles, it does not eliminate all of the problems associated with hypodermic syringes. Health care personnel and others working in the health care environment still frequently stick themselves with the needles before, during and after they are used.

Needle sticks commonly occur when the user of the syringe attempts to put the cap back on the needle after it is used. Health care providers tend to recap needles to protect themselves, to alleviate patient fear and the like. Placing a conventional needle cap on a needle without scratching or pricking fingers can be difficult, particularly in the often stressful nature of health care environments.

Needle sticks also commonly occur when the needle must be removed from the syringe. There are many circumstances in which a used needle must be removed and replaced with a different needle before the syringe can be discarded. For example, when a blood culture is performed, the needle used for removing blood from a patient must be removed and replaced with a clean needle prior to transferring the blood from the syringe to the sterile culture bottle. Small needles used to withdraw blood from patients with small veins are often replaced with larger needles to prevent destruction of the blood cells upon transfer of the blood from the syringe to another container. In other cases, needles large enough to transfer the medication from the original container to the syringe are replaced by smaller needles required for certain procedures, e.g., controlled applications of anesthesia in repairing a wound. Removal of the needle directly by hand exposes the hand to contamination and often results in a needle stick. Of course, recapping the needle prior to its removal can also lead to a needle stick. Although instruments such as hemostats can be used to remove the needle, they have to be sterilized after they are used resulting in added time and expense. Also, such instruments are not always available when removal of the needle is required.

In addition, there are certain procedures associated with hypodermic syringes that currently require the user to work with his or her fingers and hands in very close proximity to the sharp end of the needle. For example, to inject medication into the medication port of equipment such as 3-way stop-cocks and Heparin locks, the user of the syringe must hold the relatively small medication port or attached equipment in one hand while using the other hand to maneuver the syringe and guide the exposed needle into the medication port. Any sudden movements by the patient or other disturbances can cause the user to miss the medication port with the needle and stick his or her hand or finger rendering the needle and medication contaminated.

Finally, health care personnel and others associated with health care environments are frequently stuck by needles that have been improperly discarded or inadvertently left lying on a work surface, dropped on the floor, etc.

In an attempt to prevent accidental needle sticks, many hospitals and other health care facilities have adopted policies that prohibit the practice of recapping needles after they are used. In addition, hypodermic syringes have been developed that include protective devices such as tubular shields that can be extended over the needle. Unfortunately, policies prohibiting needle recapping and protective needle shields do not prevent needle sticks when the needle has to be removed and when the syringe is used in connection with procedures that require use of the user's fingers and hands in close proximity to the needle. Needle shields must usually be retracted before the needle can be removed from the syringe or inserted into the medication ports of most medical equipment.

SUMMARY OF THE INVENTION

In accordance wiring the present invention, an improved safety syringe is provided. The safety syringe comprises:

(a) a syringe body including an exterior surface, first and second opposing ends and an interior cavity extending from said first end to said second end, the second end of the syringe body being adapted for attachment to a needle;

(b) a piston member slidably disposed in the interior cavity of the syringe body between the first and second ends of the syringe body;

(c) an extension arm extending from the piston member through the first end of the syringe body, the extension arm including a first end portion attached to the piston member, a second end portion opposing the first end portion, and an elongated arm portion connecting the first and second end portions together; and (d) a needle remover removably attached to the extension arm adapted for grasping a needle removably attached to the second end of the syringe body and removing the needle from the syringe body.

In one embodiment, the safety syringe further comprises a needle removably attached to the syringe body and including a proximal end attached to the second end of the syringe body, a distal pointed end and an interior passage extending from the proximal end to the distal end, the interior passage being in fluid communication with the interior cavity of the syringe body. In another embodiment, the extension arm further includes a portion having a cavity disposed therein, and the needle remover is removably disposed in the cavity of the extension arm. In yet another embodiment, a needle shield is attached to the syringe body and movable with respect to the syringe body from a retracted position away from the distal end of the needle whereby the distal end of the needle is exposed to an extended position over the distal end of the needle whereby the distal end of the needle is shielded. The needle shield operates in conjunction with the needle remover to prevent dangerous exposure of the needle in all applications.

It is, therefore, an object of the invention to provide a safety syringe that prevents dangerous exposure of the needle and resulting accidental needle sticks in all applications.

It is an object of the invention to provide a syringe that includes apparatus for removing the needle after the needle is used, as an integral part thereof.

It is an object of the invention to provide a syringe that includes both apparatus for shielding the needle before, during and after use of the needle and apparatus for removing the needle after it is used.

It is an object of the invention to provide a syringe that prevents exposure of the needle and accidental needle sticks as a result thereof even when the syringe is used in association with medical equipment such as 3-way stop-cocks and Heparin locks.

Other and further objects, features and advantages of the present invention will be readily apparent to those skilled in the art upon a reading of the description of the preferred embodiments which follows when taken in conjunction with the accompanying drawings.

DETAILED DESCRIPTION OF THE PREFERRED EMBODIMENTS

Although the safety syringe of the present invention is useful in other applications such as applications involving the transfer of radioactive material, it is specifically designed for use as a hypodermic syringe. The safety features of the syringe protect users of the syringe and other people coming into contact therewith from accidental punctures with the needle. As used herein and in the appended claims, a hypodermic syringe is any syringe or similar device that can be used with a hypodermic needle to inject or withdraw a substance. Examples of such syringes or devices include conventional hypodermic syringes for injecting medications, phlebotomy tubes, intravenous catheter placement units and the like. A hypodermic needle is a hollow needle for injecting and/or withdrawing a substance into or from a human or animal body (subcutaneously, intramuscularly, etc.).

Referring now to the drawings and particularly to FIGS. 1-5, the safety syringe of the present invention is illustrated and generally designated by the numeral 20. The safety syringe 20 includes a syringe body 22, a hypodermic needle 23, a piston member 24, an extension arm 26, a needle remover 28 and a needle shield 30.

Figures 1, 2, 3, 4:
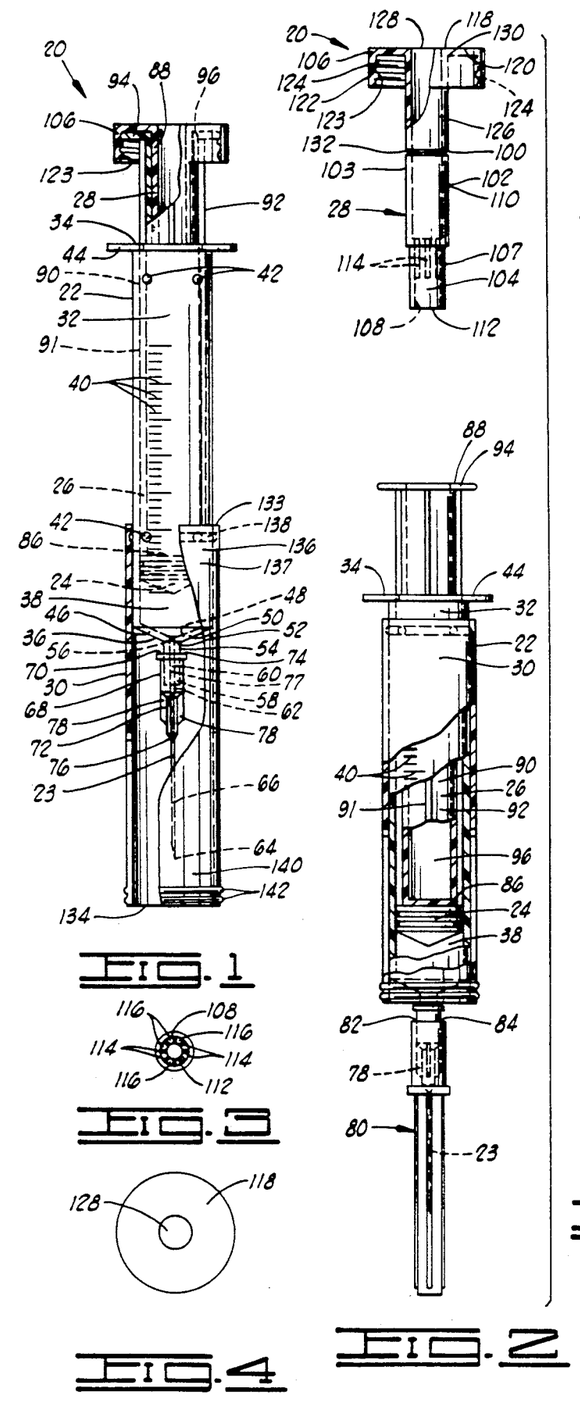
FIG. 1 is a side elevational view of a preferred embodiment of the safety syringe of the present invention with the needle remover stored in the extension arm and the needle shield in the extended position.
FIG. 2 is a side elevational view of the safety syringe of FIG. 1 with the needle remover apart from the syringe and the needle shield in the retracted position.
FIG. 3 is a view of the second end of the needle remover of the safety syringe of FIGS. 1 and 2.
FIG. 4 is a view of the first end of the needle remover of the safety syringe of FIGS. 1 and 2.
Figure 5:
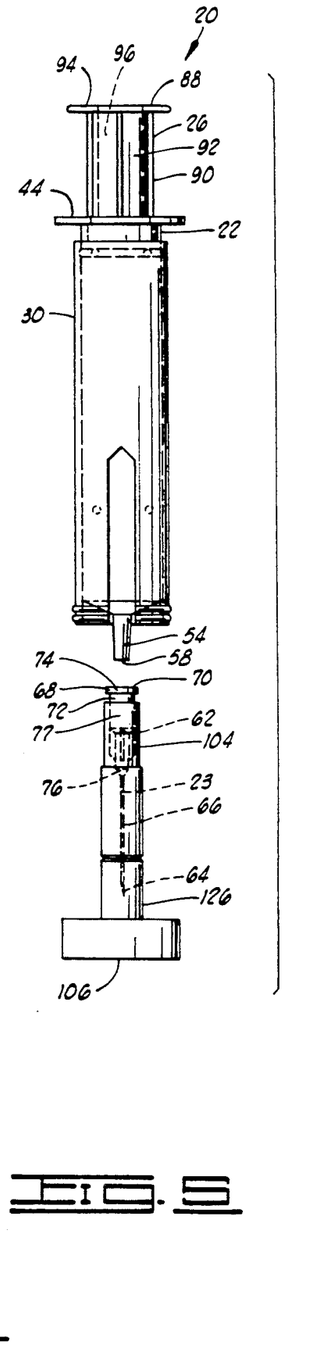
FIG. 5 is a side elevational view of the safety syringe of FIGS. 1 and 2 illustrating use of the needle remover to remove the needle from the syringe.

The syringe body 22 is an elongated, cylindrical member including an exterior surface 32, a first end 34, a second end 36 spaced from and opposing the first end 34 and an interior cavity 38 extending from the first end 34 to the second end 36. The interior cavity 38 is for containing the substance to be withdrawn and/or injected. The exterior surface 32 contains graduations or indicia 40 for indicating the volume of fluid in the interior cavity 38. Locking protuberances 42 are disposed on the exterior surface 32 for engaging with and locking the needle shield 30 in various positions with respect to the syringe body 22.

The first end 34 of the syringe body 22 is open so that the extension arm 26 can extend therethrough. A flange or finger grip 44 is attached to the exterior surface 32 of the syringe body 22 adjacent the first end 34 for facilitating use of the piston member 24 and extension arm 26 to withdraw and/or inject the substance. The second end 36 of the syringe body 22 is spaced from and opposes the first end 34. The second end 36 includes a wall 46 having a circular concavo-convex shape with a concave interior surface 48 and convex exterior surface 50. An opening 52 is disposed in the center of the wall 46, and a nipple member 54 for receiving the needle 23 is disposed on the convex exterior surface 50 over the opening 52. The nipple member 54 includes an open proximal end 56 positioned over the opening 52, a reduced distal end 58 spaced from and opposing the proximal end 56 and an interior axial passage 60 extending between the proximal and distal ends 56 and 58. The axial passage 60 is in fluid communication with the interior cavity 38 of the syringe body 22. When stated herein and in the appended claims that one element is in fluid communication with one or more other elements, it is meant that the one element is attached to the other element(s), directly or indirectly, in a way that allows fluid to flow from the one element to the other element(s).

The hypodermic needle 23 is an elongated, hollow conventional hypodermic needle. Conventional hypodermic needles are typically sold separately from conventional hypodermic syringes. The needle 23 is removably attached to the syringe body 22 and includes a proximal end 62, a distal pointed end 64 spaced from and opposing the proximal end 62, an interior passage 66 extending from the proximal end 62 to the distal end 64 and a hub member 68. The hub member 68 is a tubular member that connects the proximal end 62 of the needle 23 to the distal end 58 of the nipple member 54. The hub member 68 includes an interior surface 70, an exterior surface 72, an open first end 74, a second end 76 attached over the proximal end 62 of the needle 23 and an interior axial passage 77 extending between the first end 74 and second end 76. The open first end 74 receives the distal end 58 of the nipple member 54. The interior passage 66 of the needle 23 is in fluid communication with the axial passage 77 of the hub member 68, the axial passage 60 of the nipple member 54 and the interior cavity 38 of the syringe body 22. A plurality of elongated ribs 78 are circumferentially disposed on the exterior surface 72 of the hub member 68 along the longitudinal axis thereof and extend outwardly therefrom. As discussed below, the ribs 78 are engaged by the needle remover 28 when the needle remover is used to remove the needle 23. The distal end 64 of the needle 23 is sharpened to facilitate insertion of the needle into medicine vials, medicine equipment, human and animal bodies, etc.

As shown in FIG. 2, a conventional needle cap 80 in the form of a hollow tube having an open end 82 and an interior surface 84 is attached over the needle 23. The cross-sectional diameter of the open end 82 along the longitudinal axis of the needle cap 80 is of a size sufficient to cause the interior surface 84 to grip the exterior surface 72 of the hub member 68 of the needle 23 when the needle cap is placed over the needle.

The piston member 24 is a conventional piston member slidably disposed in the interior cavity 38 of the syringe body 22 between the first end 34 and second end 36 of the syringe body. On its axis that is parallel with the longitudinal axis of the syringe body 22, the piston member 24 has a circular cross-section with a cross-sectional diameter of a size sufficient to cause the piston member to act as a seal between the first end 34 and second end 36 of the syringe body 22. Movement of the piston member 24 toward the second end 36 of the syringe body 22 forces any fluid (medicine, blood, etc.) therebetween through the opening 52 in the wall 46, though the axial passage 60 of the nipple member 54, through the axial passage 77 of the hub member 68 and through the interior passage 66 of the needle 23. Similarly, movement of the piston member 24 away from the second end 36 of the syringe body 22 creates a vacuum in the interior cavity 38 of the syringe body sufficient to draw a fluid through the interior passage 66 of the needle 23, axial passage 77 of the hub member 68, axial passage 60 of the nipple member 54 and opening 52 in the wall 46.

The extension arm 26 is an elongated member extending from the piston member 24 through the first end 34 of the syringe body 22. The extension arm 26 includes a first end portion 86 attached to the piston member 24, a second end portion 88 opposing the first end portion 86, an elongated arm portion 90 having a longitudinal axis 91 and connecting the first and second end portions 86 and 88 together, an exterior surface 92, a thin circular finger grip or flange 94 attached to the exterior surface 92 adjacent the first end portion 86 and an elongated cavity 96 having a circular longitudinal cross-section and extending through the first end portion 86 into the elongated arm portion 90 along the longitudinal axis 91 thereof. As best shown in FIGS. 1 and 2, the needle remover 28 is removably attached to the extension arm 26 by being removably disposed and stored in the cavity 96 of the extension arm.

The needle remover 28 is adapted for grasping the needle 23 and removing the needle from the syringe body 22. The needle remover 28 is an elongated member that includes a first end section 100, a second end section 102 opposing the first end section 100, an arm section 103 connecting the end sections 100 and 102 together, a needle grasp member 104 attached to the second end section 102 for grasping the needle and a connecting cap 106 removably attached to the first end section 100.

The grasp member 104 of the needle remover 28 can be any tool capable of grasping the needle 23 and removing it from the syringe body 22. For example, the grasp member 104 can be of a plier- or clamp-type structure that can be manipulated to grasp the exterior surface of the needle 23. In the preferred embodiment, the embodiment shown in the drawings, the grasp member 104 is a hollow tube including a longitudinal axis 107, an interior surface 108, a first end 110 attached to the second end section 102 of the needle remover 28 and a second end 112 opposing the first end. The second end 112 is open for receiving and grasping the exterior surface 72 of the hub member 68 of the needle 23 when the grasp member 104 is placed over the needle. As best shown by FIG. 3, a plurality of elongated teeth 114 are circumferentially disposed on the interior surface 108 of the grasp member 104 along the longitudinal axis 107 thereof. The teeth 114 are arranged to form a plurality of grooves 116 therebetween that receive the ribs 78 disposed on the exterior surface 72 of the hub member 68. The longitudinal cross-sectional diameter of the open second end 112 and the longitudinal cross-sectional internal diameter of the grasp member 104 are of a size such that when the grasp member is placed over the needle 23, at least a portion of the interior surface 108 fits snugly on at least a portion of the exterior surface 72 of the hub member 68, the grooves 116 receive the ribs 78 and the teeth 114 engage in a locking relationship with the ribs whereby rotation of the needle remover 28 rotates the hub member with respect to the nipple member 54 allowing the needle to be removed from the syringe body 22.

The connecting cap 106 includes a circular end wall 118 having an inside surface 120, an annular side wall 122 perpendicularly extending outwardly from the inside surface 120 and having an inside surface 123, locking means in the form of threads 124 disposed on the inside surface 123 and an elongated, hollow guide tube 126 attached to the inside surface 120 and perpendicularly extending outwardly therefrom. As best shown by FIG. 4, the inside surface 120 of the end wall 118 includes a circular opening 128 disposed therein. The guide tube 126 has a first open end 130 attached to the inside surface 120 directly over the opening 128 therein, and a second open end 132 removably attached to the first end section 100 of the needle remover 28. The grasp member 104, end sections 100 and 102, arm section 103 and guide tube 126 can be integrally formed as a single hollow tube if desired. In an alternate embodiment, the connecting cap 106 does not include the guide tube 126 and the inside surface 120 of the connecting cap is removably attached directly to the first end section 100 of the needle remover. As discussed below, the second open end 132 of the guide tube 126, or in the alternate embodiment the inside surface 120 of the connecting cap 106, can be detached from the first end section 100 of the needle remover, and the connecting cap can be attached to the needle shield 30 and used in association with Heparin locks and other medical equipment.

As illustrated in FIG. 1, the threads 124 disposed on the inside surface 123 of the side wall 122 of the connecting cap 106 allow the connecting cap to be threaded onto the flange 94 of the extension arm 26 to lock the needle remover 28 in the cavity 96 of the extension arm. As discussed further below, the threads 124 also allow the connecting cap 106 to be locked onto the needle shield 30 for use in certain applications. The cross-sectional diameter of the connecting cap 106 is of a size sufficient to allow the connecting cap to thread onto the flange 94 and needle shield 30.

The needle shield 30 is an elongated cylindrical tube having a longitudinal cross-sectional internal diameter slightly greater than the longitudinal cross-sectional external diameter of the syringe body 22. The needle shield 30 is slidably attached to the exterior surface 32 of the syringe body 22 over the syringe body and is movable with respect to the syringe body from a retracted position away from the distal end 64 of the needle 23 whereby the distal end of the needle is exposed (as shown by FIG. 2) to an extended position over the distal end of the needle whereby the distal end of the needle is shielded (as shown by FIG. 1). The needle shield 30 includes a first end part 133 attached to the exterior surface 32 of the syringe body 22, a second end part 134 opposing the first end part and spaced from the first end part toward the distal end 64 of the needle 23, a middle part 136 extending around the syringe body and connecting the first and second end parts together and an exterior surface 137. An elongated slit 138 is disposed in the middle part 136 along the horizontal axis thereof adjacent the first end part 133 for engaging with the locking protuberances 42 disposed on the exterior surface 32 of the syringe body 22 to lock the needle shield 30 in retracted and extended positions. A pair of elongated slits 140 are disposed in the needle shield 30 on opposite sides along the longitudinal axis thereof. Each of the slits 140 extends through the second end part 134 into the middle part 136 of the needle shield 30 and, as discussed below, allow the needle shield to be used in association with 3-way stop-cocks and other medical equipment. Locking means in the form of a plurality of threads 142 are disposed on the exterior surface 137 of the needle shield 30 adjacent the second end part 134 for engaging with the threads 124 of the connecting cap 106 to lock the connecting cap onto the second end part of the needle shield. The needle shield 30 is made out of transparent material so that the graduations or indicia 40 disposed on the exterior surface 32 of the syringe body 22 can be utilized even when the shield is in a retracted position. The length of the needle remover 28 is such that when the needle shield 30 is locked in the fully extended position, the grasp member 104 can be positioned over the needle 23 and in contact with the hub member 68 and the connecting cap 106 can be threaded onto the needle shield over the second end part 134 thereof. This arrangement provides a double shield over the needle with the needle remover acting as a reinforcing brace holding the needle shield in the extended position. If desired, the needle shield 30 can be made to irreversibly lock in the extended position and the connecting cap 106 can be made to irreversibly lock onto the needle shield to prevent access to the needle 23 after the syringe is discarded.

Referring now to the drawings, and particularly to FIGS. 5-10, use of the safety syringe 20 will be described. To remove a contaminated needle 23 from the syringe body 22, the needle remover 28 must first be detached from the extension arm 26. The connecting cap 106 is turned counterclockwise to unthread it from the flange 94 and the needle remover 28 is pulled out of the cavity 96. With the needle shield 30 in an extended position covering the distal end 64 of the needle 23, the grasp member 104 of the needle remover 28 is inserted over the needle and into contact with the hub member 68 of the needle. The needle remover 28 is then rotated in a clockwise direction and pulled away from the syringe body 22 to remove the needle 23. The entire needle remover 28 with the contaminated needle 23 therein can then be discarded. Alternatively, the needle remover 28 with the contaminated needle 23 therein can be placed and locked back in the cavity 96 of the extension arm, and the entire syringe 20 can ultimately be discarded.

The needle remover 28 is an integral part of the syringe 22 and is therefore always available when needed. Policies requiring the use of hemostats or other tools to remove the needle are difficult to abide by because such tools are not always present when needed. Also, hemostats and other tools typically do not shield the needle after it is removed.

Figures 6, 7, 8, 9:
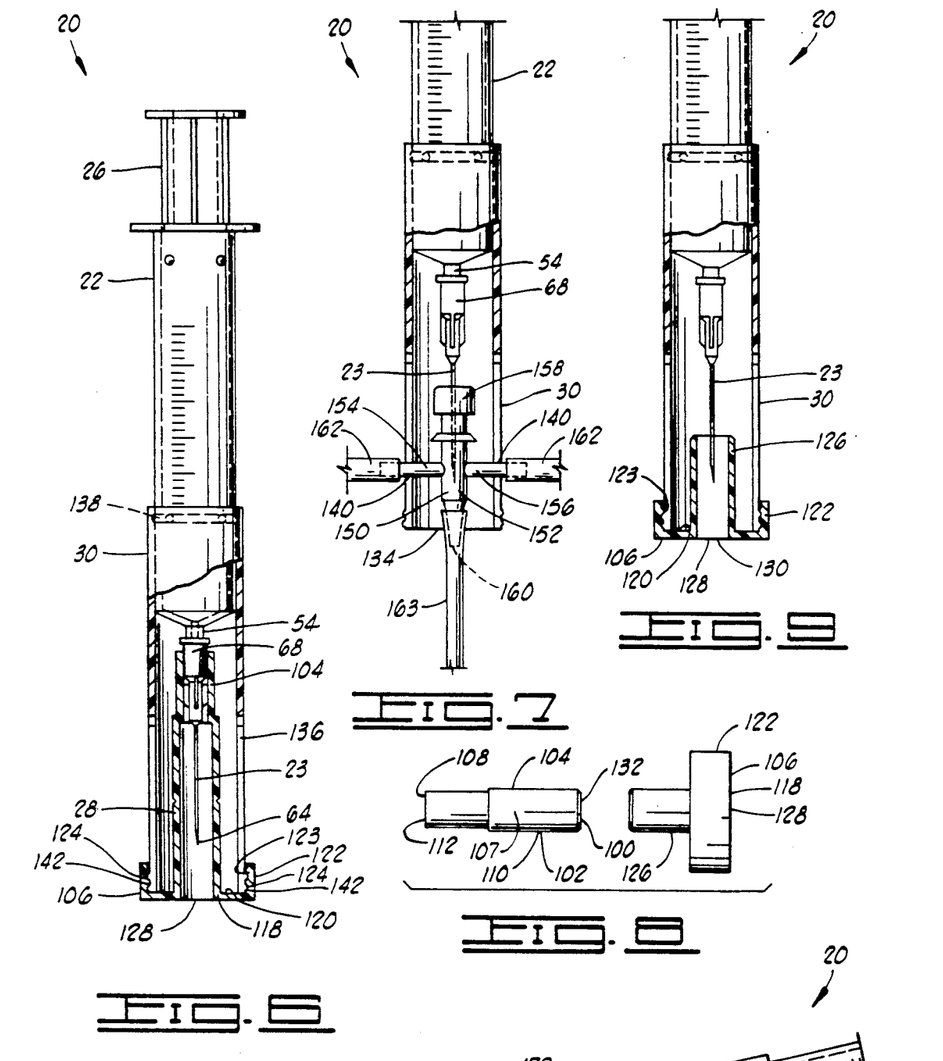
FIG. 6 is a side elevational view of the safety syringe of FIGS. 1 and 2 illustrating use of the needle remover and needle shield to fully shield the needle.
FIG. 7 is a partial side elevational view of the safety syringe of FIGS. 1 and 2 illustrating use of the syringe in association with a 3-way stop-cock.
FIG. 8 is a side elevational view of the needle remover of the safety syringe of FIGS. 1 and 2 illustrating separation of the connecting cap therefrom.
FIG. 9 is a partial side elevational view of the safety syringe of FIGS. 1 and 2 illustrating attachment of the separated connecting cap of the needle remover to the second end of the needle shield.

The needle remover 28 prevents people coming into contact with the disposed needle 23 after it is removed from being stuck thereby. Even when it is not necessary to remove the needle 23 from the syringe body 22, the needle remover 28 can be used with the needle shield 30 to provide double protection. When the needle shield 30 is fully extended, it will cover the distal end 64 of the needle 23. As best shown by FIG. 6, with the needle shield 30 in the fully extended position, the grasp member 104 of the needle remover 28 can be placed over the needle 23 and into contact with the hub member 68 without removing the needle. The connecting cap 106 can then be threaded onto the exterior surface 137 over the second end part 134 of the needle shield 30 to lock the needle remover 28 in position over the needle 23. In this position, the needle remover 28 serves as a reinforcing brace holding the needle shield 30 in the extended position making it virtually impossible for the needle 23 to inadvertently become exposed.

The needle shield 30 can be left in the fully extended position when the needle 23 is inserted into blood or medicine vials to transfer blood or medicine therefrom in order to prevent the blood or medicine from being splashed or sprayed onto the user. The needle shield 30 can also be left in the fully extended position when the user is carrying the syringe from the location of the medicine vial, etc. to a patient to be injected. This helps to prevent contamination of the needle and medication and to alleviate patient fear, etc. For added protection, the needle shield can be put over the needle during this time if desired.

Use of the safety syringe 20 in connection with a 3-way stop-cock is illustrated by FIG. 7. A 3-way stop-cock is a medical device that allows three separate fluids or medications to be introduced into a patient through a single intraveneously positioned needle. The 3-way stop-cock, designated by the numeral 150 in FIG. 7, includes a valve 152 having a first tubular entry port 154, a second tubular entry port 156, a medication injection port 158 and an outlet 160. One or more fluids or medications can be intraveneously introduced into the patient through the tubular entry ports 154 and 156, and a fluid or medication can be intraveneously injected into the patient through the medication injection port 158. Fluid or medication inlet tubes 162 extend from a source of the fluids or medications to the entry ports 154 and 156. A tube or conduit 163 is connected to the outlet 160 to transfer the fluid(s) and/or medication(s) to a needle positioned intraveneously in the patient (not shown). To inject a fluid or medication through the medication injection port 158, the user is required to hold the 3-way stop-cock 150 in one hand while maneuvering the syringe 20 to guide the needle 23 into the medication port with the other hand. Due to their close proximity to the needle, the fingers and hand of the user holding the 3-way stop-cock are very susceptible to needle sticks during this procedure.

As illustrated by FIG. 7, the needle shield 30 can be used to prevent needle sticks when the syringe 20 is used to inject a fluid or medication into the medication injection port in a 3-way stop-cock. With the needle shield 30 in a fully extended position, the 3-way stop-cock 150 is merely inserted into the needle shield 30 until the needle 23 makes contact with and is inserted into the medication injection port 158. The first and second tubular entry ports 154 and 156 and corresponding inlet tubes 162 extend through the slits 140 in the needle shield. This allows the needle and corresponding fluid or medication to be introduced into the 3-way stop-cock 50 without exposing the needle to the user.

Figure 10:
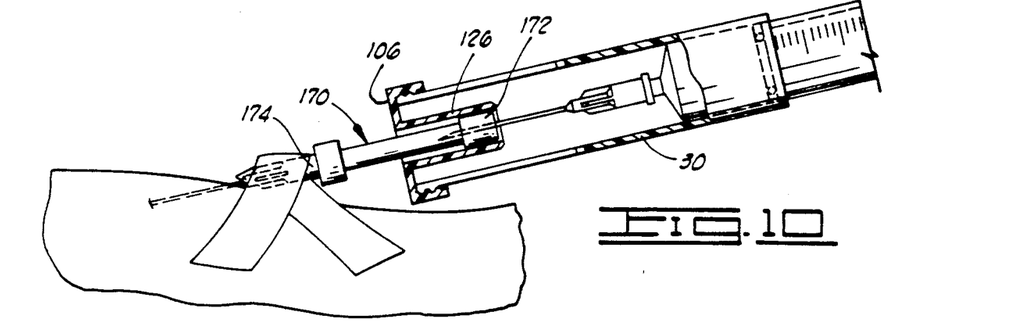
FIG. 10 is a partial perspective/side elevational view of the safety syringe of FIGS. 1 and 2 illustrating use of the syringe in association with a Heparin lock.

Similarly, as illustrated by FIGS. 8-10, the safety syringe 20 can be used to safely inject a fluid or medication into a Heparin lock without exposing the needle to the user. A Heparin lock is a medical device that is intraveneously inserted into patients that require routine blood tests and/or administration of medication but not a constant supply of fluids and/or medications through a conventional intraveneous set up. The Heparin lock, designated by the numeral 170 in FIG. 10, comprises a medication injection port 172 and an outlet 174. The outlet 174 is attached to a needle that is intraveneously positioned in the patient. Like 3-way stopcocks, Heparin locks require health care personnel to hold the device in one hand while using the other hand to maneuver the syringe and guide the needle into the medication port. Due to their close proximity to the needle, the fingers and hand of the user are particularly susceptible to needle sticks during this procedure.

The needle shield 30 and connecting cap 106 of the needle remover 28 of the safety syringe 22 can be used to prevent needle sticks when the syringe is used to inject a fluid or medication into a Heparin lock. First, as illustrated by FIG. 8, the connecting cap 106 is detached from the first end section 100 of the needle remover 28. As best shown by FIG. 9, the connecting cap 106 is then threaded onto the needle shield 30 over the second end part 34 thereof with the guide tube 126 of the connecting cap extending into the shield over the distal end 64 of the needle 23. As shown by FIG. 10, the medication injection port 172 of the Heparin lock can be inserted through the circular opening 128 in the end wall 118 and through the guide tube 126 of the connecting cap 106 until the needle 23 makes contact with and is inserted therein. The guide tube 126 guides the medication port 172 to the needle 23. The fluid or medication is then injected into the medication port and patient, and the syringe 22 is pulled away from the Heparin lock to remove the needle and syringe therefrom. Neither the user nor the patient is exposed to the needle during this procedure.

Thus, the needle remover 28 and needle shield 30 operate individually and together to prevent exposure of the needle during virtually any application of the syringe. The safety syringe of the present invention is well adapted to carry out the objects and attain the ends and advantages mentioned as well as those inherent therein. While numerous changes in the arrangement and construction of parts will suggest themselves to those skilled in the art, such changes are encompassed within the scope of this invention as defined by the appended claims.

What is claimed is:

1. A safety syringes comprising:
   a syringe body including an exterior surface, first and second opposing ends and an interior cavity extending from said first end to said second end;
   a needle removably attached to said syringe body and including a proximal end attached to said second end of said syringe body, a distal pointed end spaced from and opposing said proximal end, and an interior passage extending from said proximal end to said distal end, said interior passage being in fluid communication with said interior cavity of said syringe body;
   a piston member slidably disposed in said interior cavity of said syringe body between said first and second ends of said syringe body;
   an extension are extending from said piston member through said first end of said syringe body, said extension arm including a first end portion attached to said piston member, a second end portion opposing said first end portion, and an elongated arm portion connecting said first and second end portions together;
   a needle shield attached to said syringe body and movable with respect to said syringe body from a retracted position away from said distal end of said needle whereby said distal end of said needle is exposed to an extended position over said distal end of said needle whereby said distal end of said needle is shielded, said needle shield including a first end part attached to said exterior surface of said syringe body, a second end part opposing said first end part and spaced from said first end part toward said distal end of said needle, and a middle part extending around said syringe body and connecting said first and second end parts together; and
   a needle remover removably attached to said extension arm adapted for grasping said needle and removing said needle from said syringe body, said needle remover being an elongated member including a first end section, a second end section opposing said first end section, an arm section connecting said first and second end sections together and a grasp member attached to said second end section for grasping said needle, and being of a length sufficient to grasp said needle when said needle shield is moved to said extended position over said distal end of said needle without extending completely within said needle shield.

2. The safety syringe of claim 1 wherein said middle part of said needle shield has at least one opening disposed therein for allowing medical equipment to pass through said needle shield toward said needle, the opening extending through the second end part into the middle part of the needle shield.

3. The safety syringe of claim 2 wherein said middle part of said needle shield has a pair of slits oppositely disposed therein for allowing medical equipment to pass through opposite sides of said needle shield toward said needle, each of said slits extending through said second end part into said middle part of said needle shield.

4. The safety syringe of claim 1 wherein said grasp member is a hollow tube including an interior surface, a first end attached to said second end section of said needle remover and a second end opposing said first end, said second and of said hollow tube being open for receiving and grasping said needle.

5. The safety syringe of claim 4 wherein:
said needle further includes an exterior surface and a plurality of ribs disposed on said exterior surface and extending outwardly therefrom;
said grasp member of said needle remover further includes a plurality of teeth disposed on said interior surface of said grasp member for receiving and engaging in a locking relationship with said ribs of said needle; and
said needle remover is of a length sufficient for said teeth of said grasp member to receive and engage in a locking relationship with said ribs of said needle when said needle shield is moved to said extended position over said distal end of said needle without extending completely within said needle shield.

6. The safety syringe of claim 1 wherein:
said extension arm includes a portion having an elongated cavity disposed therein, said cavity of said extension arm extending through said second end portion of said extension arm into said elongated arm portion of said extension arm; and
said needle remover is removably disposed in said cavity of said extension arm.

7. The safety syringe of claim 6 wherein said needle remover further includes a connecting cap removably attached to said first end section of said needle remover and attachable to and over said second end part of said needle shield, said connecting cap including an end wall having an inside surface attached to said first end section, a side wall perpendicularly extending outwardly from said inside surface of said end wall and having an inside surface, and locking means disposed o said inside surface of said wall for engaging with said extension arm to lock said needle remover in said cavity of said extension arm and for engaging with said second end part of said needle shield to lock said connecting cap over said second end part of said needle shield.

8. The safety syringe of claim 7 wherein said end wall of said connecting cap further includes an opening therein for allowing medical equipment to pass through said connecting cap.

9. The safety syringe of claim 8 wherein said connecting cap further includes an elongated hollow guide tube attached to said inside surface of said end wall and perpendicularly extending outwardly therefrom, said guide tube having a first open end attached to said inside surface of said end wall directly over said opening therein and a second open end removably attached to said first end section of said needle remover.

10. Safety syringe comprising:
a cylindrical syringe body including an exterior surface, first and second opposing ends and an interior cavity extending from said first end to said second end;
a needle removably attached to said syringe body and including a proximal end attached to said second end of said syringe body, a distal pointed end spaced from and opposing said proximal end and an interior passage extending from said proximal end to said distal end, said interior passage being in fluid communication with said interior cavity of said syringe body;
a piston member slidably disposed in said interior cavity of said syringe body between said first and second ends of said syringe body;
an extension arm extending from said piston member through said first end of said syringe body, said extension arm having a first end portion attached to said piston member, a second end portion opposing said first end portion, and an elongated arm portion connecting said first and second end portions together;
a cylindrical needle shield slidably attached over said syringe body and movable with respect to said syringe body from a retracted position away from said distal end of said needle whereby said distal end of said needle is exposed to an extended position over said distal end of said needle whereby said distal end of said needle is shielded, said needle shield including a first end part attached to said exterior surface of said syringe body, a second end part opposing said first end part and spaced from said first end part toward said distal end of said needle, and a middle part extending around said syringe body and connecting said first and second end parts together; and
a connecting cap removably attached to said syringe and attachable to said second end part of said needle shield, said connecting cap including an end wall having an inside surface and having an opening for allowing medical equipment to pass through said connecting cap, a side wall perpendicularly extending outwardly from said inside surface of said end wall and having an inside surface, and locking means disposed on said inside surface of said side wall for engaging with said second end part to lock said connecting cap over said second end part.

11. The safety syringe of claim 10 wherein said connecting cap further includes an elongated hollow guide tube attached to said inside surface of said end wall and perpendicularly extending outwardly therefrom, said guide tube having a first open end attached to said inside surface of said end wall directly over said opening in said end wall and a second open end opposing and spaced from said first open end.

12. The safety syringe of claim 10 wherein said needles shield further includes a part having at least one slit disposed therein for allowing medical equipment to pass through said needle shield toward said needle, said slit extending through said second end part into said middle part of said needle shield.

13. The safety syringe of claim 10 wherein said needle shield further includes a part having a pair of slits oppositely disposed therein for allowing medical equipment to pass through opposite sides of said needle shield toward said needle, each of said slits extending through said second end part into said middle part of said needle shield.

14. The safety syringe of claim 10 further comprising a needle remover removably attached to said extension arm adapted for grasping said needle and removing said needle from said syringe body.

15. The safety of claim 14 wherein said needle remover is an elongated member of a length sufficient to grasp said needle when said needle shield is moved to said extended position over said distal end of said needle without extending completely within said needle shield and includes a first end section, a second end section opposing said first end section, an arm section connecting said first and second end sections together and a grasp member attached to said second end section for grasping said needle.

16. The safety syringe of claim 15 wherein said grasp member is a hollow tube including an interior surface, a first end attached to said second end section of said needle remover and a second end opposing said first, end, said second end of said hollow tube being open for receiving and grasping said needle.

17. The safety syringe of claim 16 wherein:
said needle further includes an exterior surface and a plurality of ribs disposed on said exterior surfaced and extending outwardly therefrom;
said grasp member of said needle remover further includes a plurality of teeth disposed on said interior surface of said grasp member for receiving and engaging in a locking relationship with said ribs of said needle; and
said needle remover is of a length sufficient for said teeth of said grasp member to receive and engage in a locking relationship with said ribs of said needle when said needle shield is moved to said extended position over said distal end of said needle without extending completely within said needle shield.

18. The safety syringe of claim 14 wherein:
said extension arm includes a portion having an elongated cavity disposed therein, said cavity of said extension arm extending through said second end portion of said extension arm into said elongated portion of said extension arm; and
said needle remover is removably disposed in said cavity of said extension arm.

* * * * *

UNITED STATES PATENT AND TRADEMARK OFFICE
CERTIFICATE OF CORRECTION

PATENT NO. : 5,088,985

DATED : February 18, 1992

INVENTOR(S) : Marco A. Deras

It is certified that error appears in the above—identified patent and that said Letters Patent is hereby corrected as shown below:

Column 1, line 24, delete the period after "(aids)" and substitute a comma therefor;

Column 2, line 35, delete "wiring" and substitute --with-- therefor;

Column 10, line 25, delete "are" and substitute --arm-- therefor;

Column 11, line 41, delete "o" and substitute --on-- therefor;

Column 11, line 59, insert --A-- before "Safety";

Column 13, line 10, delete the comma after "first" (at the end of the line); and Column 13, line 15, delete "surfaced" and substitute --surface-- therefor.

Signed and Sealed this

Twentieth Day of April, 1993

Attest:

MICHAEL K. KIRK

*Attesting Officer*     Acting Commissioner of Patents and Trademarks